(12) United States Patent
Ansley et al.

(10) Patent No.: US 10,294,935 B2
(45) Date of Patent: May 21, 2019

(54) REMOVABLE CARTRIDGE FOR LIQUID DIFFUSION DEVICE

(71) Applicant: Prolitec Inc., Milwaukee, WI (US)

(72) Inventors: Matthew Ansley, Muskego, WI (US); Nathan Sward, Milwaukee, WI (US); Howard Tanner, Wauwatosa, WI (US)

(73) Assignee: Prolitec Inc., Milwaukee, WI (US)

( * ) Notice: Subject to any disclaimer, the term of this patent is extended or adjusted under 35 U.S.C. 154(b) by 0 days.

(21) Appl. No.: 15/711,930

(22) Filed: Sep. 21, 2017

(65) Prior Publication Data

US 2018/0100498 A1 Apr. 12, 2018

Related U.S. Application Data

(63) Continuation of application No. 14/835,438, filed on Aug. 25, 2015, now Pat. No. 9,797,396, which is a (Continued)

(51) Int. Cl.
*B01F 3/04* (2006.01)
*F04B 53/00* (2006.01)
(Continued)

(52) U.S. Cl.
CPC .............. *F04B 53/003* (2013.01); *A61L 9/14* (2013.01); *A61L 9/145* (2013.01); *A61M 11/02* (2013.01);
(Continued)

(58) Field of Classification Search
CPC ...... A61L 9/14; A61L 9/145; A61L 2209/134; A61M 11/02; B01F 3/04007;
(Continued)

(56) References Cited

U.S. PATENT DOCUMENTS

RE24,291 E 3/1957 Goodyer
4,007,238 A * 2/1977 Glenn ..................... A61M 11/06
128/200.18
(Continued)

FOREIGN PATENT DOCUMENTS

EP 0135390 A2 * 3/1985
GB 726916 A 3/1955

OTHER PUBLICATIONS

Australian Office Action, dated Dec. 7, 2017, for Australian Application No. 2015250094, 3 pages.
(Continued)

*Primary Examiner* — Charles S Bushey
(74) *Attorney, Agent, or Firm* — Seed IP Law Group LLP

(57) ABSTRACT

A removable cartridge for use with a liquid diffusion device is provided. The removable cartridge includes a cartridge housing defining an internal housing cavity, partially filled with a liquid to be diffused, and a diffusion head positioned within the internal housing cavity with a venturi device for generating diffused liquid from the liquid contained in the internal housing cavity. The diffusion head defines at least a portion of a gas supply conduit that extends from a bottom end of the removable cartridge to the venturi device through the liquid to be diffused to enable the venturi device to be supplied with pressurized gas from an external source via the bottom end of the removable cartridge.

16 Claims, 8 Drawing Sheets

Related U.S. Application Data continuation of application No. 14/612,066, filed on Feb. 2, 2015, now Pat. No. 9,248,461.

(60) Provisional application No. 61/982,504, filed on Apr. 22, 2014.

(51) Int. Cl.

| | |
|---|---|
| *A61L 9/14* | (2006.01) |
| *B05B 7/24* | (2006.01) |
| *F24F 3/16* | (2006.01) |
| *F04B 39/12* | (2006.01) |
| *F04B 39/00* | (2006.01) |
| *F04B 45/047* | (2006.01) |
| *A61M 11/02* | (2006.01) |
| *B05B 1/26* | (2006.01) |
| *B05B 7/00* | (2006.01) |
| *B05B 7/26* | (2006.01) |
| *B01F 5/04* | (2006.01) |
| *B01F 15/02* | (2006.01) |
| *F04B 53/16* | (2006.01) |

(52) U.S. Cl.
CPC ...... *B01F 3/04007* (2013.01); *B01F 3/04021* (2013.01); *B01F 3/0446* (2013.01); *B01F 5/0413* (2013.01); *B01F 15/0244* (2013.01); *B05B 1/26* (2013.01); *B05B 7/0012* (2013.01); *B05B 7/24* (2013.01); *B05B 7/2489* (2013.01); *B05B 7/265* (2013.01); *F04B 39/0044* (2013.01); *F04B 39/121* (2013.01); *F04B 39/127* (2013.01); *F04B 45/047* (2013.01); *F04B 53/16* (2013.01); *F24F 3/16* (2013.01); *A61L 2209/134* (2013.01); *B01F 2005/0448* (2013.01); *B01F 2215/009* (2013.01); *F24F 2003/1689* (2013.01)

(58) Field of Classification Search
CPC .. B01F 3/04021; B01F 3/0446; B01F 5/0413; B01F 15/0244; B01F 2005/0448; B01F 2215/009; B05B 7/24; B05B 7/2489; B05B 7/265; B05B 1/26; B05B 7/0012; F04B 39/0044; F04B 39/121; F04B 39/127; F04B 45/047; F04B 53/003; F04B 53/16; F24F 3/16; F24F 2003/1689
USPC .......... 261/72.1, 74, 76, 78.2, 79.2, DIG. 88
See application file for complete search history.

(56) References Cited

U.S. PATENT DOCUMENTS

| | | | |
|---|---|---|---|
| 4,190,046 A | 2/1980 | Virag | |
| 4,501,664 A | 2/1985 | Heil et al. | |
| 4,595,564 A | 6/1986 | Spector et al. | |
| 5,533,497 A * | 7/1996 | Ryder | B05B 7/0012 |
| | | | 128/200.21 |
| 6,405,944 B1 | 6/2002 | Benalikhoudja | |
| 7,036,800 B2 | 5/2006 | Ellis | |
| 7,363,737 B2 | 4/2008 | Benalikhoudja | |
| 7,377,493 B2 | 5/2008 | Thomas | |
| 7,493,898 B2 | 2/2009 | King | |
| 7,581,718 B1 * | 9/2009 | Chang | A61M 11/06 |
| | | | 128/200.18 |
| 7,712,683 B2 | 5/2010 | Robert et al. | |
| 7,930,068 B2 | 4/2011 | Robert et al. | |
| 7,950,630 B2 * | 5/2011 | Curien | A47L 9/183 |
| | | | 261/64.5 |
| 8,006,698 B2 * | 8/2011 | Boehm | A61M 11/02 |
| | | | 128/200.24 |
| 8,276,587 B2 * | 10/2012 | Zhang | A61M 11/06 |
| | | | 128/203.19 |
| 8,562,914 B2 | 10/2013 | Slutz et al. | |
| 8,596,264 B2 * | 12/2013 | Sommer | A61M 11/06 |
| | | | 128/200.14 |
| 8,602,396 B1 | 12/2013 | V et al. | |
| 8,855,827 B2 | 10/2014 | Weening et al. | |
| 8,876,086 B2 | 11/2014 | Burke et al. | |
| 9,162,004 B1 * | 10/2015 | Ansley | B01F 5/0413 |
| 9,248,461 B2 * | 2/2016 | Ansley | B01F 5/0413 |
| 9,480,767 B1 | 11/2016 | Ansley et al. | |
| 9,586,228 B2 * | 3/2017 | Roemburg | A61L 9/127 |
| 9,745,976 B2 * | 8/2017 | Ansley | B01F 5/0413 |
| 9,797,396 B2 * | 10/2017 | Ansley | F04B 53/003 |
| 2006/0219814 A1 | 10/2006 | Benalikhoudja | |
| 2006/0237090 A1 | 10/2006 | Benalikhoudja | |
| 2009/0078793 A1 | 3/2009 | Nelson et al. | |
| 2013/0049236 A1 | 2/2013 | Garon et al. | |
| 2015/0076716 A1 | 3/2015 | Roemburg et al. | |
| 2016/0175474 A1 | 6/2016 | Ansley et al. | |

OTHER PUBLICATIONS

International Preliminary Report on Patentability, dated Oct. 25, 2016, for International Application No. PCT/US2015/026257, 6 pages.

* cited by examiner

REMOVABLE CARTRIDGE FOR LIQUID DIFFUSION DEVICE

BACKGROUND

Technical Field

The present disclosure relates generally to liquid diffusion devices and, more specifically, to a removable cartridge for use with a liquid diffusion device where the liquid to be diffused is contained within the cartridge.

Description of the Related Art

Diffusion devices in the past have had the ability to dispense scent or other liquids throughout the atmosphere of desired spaces but have suffered from several drawbacks. Changing the scent or product that is being diffused has typically required that a reservoir of the diffusing device be emptied and then filled with the new liquid or scent. Conventional reservoirs may be configured to be refilled directly with the liquid to be diffused, which can be messy or have a highly concentrated odor. This refilling may not be desirably carried out in a public setting, such as a store, restaurant, casino or other commercial setting where the scent or other product may be diffused. Additionally, having to deal with bulk refills that must be poured or otherwise placed into the reservoir of the diffusion device may not be a desirable arrangement for home or non-commercial diffusion devices. An improved ability to refill or recharge a diffusion device with scent or other product is desirable.

Some diffusion devices have been developed to address the aforementioned issues by enabling a cartridge containing the liquid to be diffused to be removed from a host device upon depletion of the liquid and replaced with another like cartridge. Such diffusion devices and removable cartridges thereof, however, may be overly complex, costly and/or suffer from other deficiencies or drawbacks, such as, for example, discharging diffused liquid with less than ideal characteristics, or the cartridges being susceptible to leakage, tampering, fouling and/or contamination. Accordingly, Applicant believes that improved cartridges and cartridge components for liquid diffusion devices are desirable.

BRIEF SUMMARY

The removable cartridges for use with liquid diffusion devices and components thereof shown and described herein provide removable cartridges and cartridge components with efficient form factors that are particularly effective at treating spaces with diffused liquid having extremely small liquid particles.

At least one embodiment of a removable cartridge for use with a liquid diffusion device may be summarized as including a cartridge housing defining an internal housing cavity partially filled with a liquid to be diffused and a diffusion head positioned within the internal housing cavity, which includes a venturi device for generating diffused liquid from the liquid contained in the internal housing cavity. The diffusion head defines at least a portion of a gas supply conduit that extends from a bottom end of the removable cartridge to the venturi device through the liquid to be diffused to enable the venturi device to be supplied with pressurized gas from an external source via the bottom end of the removable cartridge.

The cartridge housing may include a plurality of housing pieces fixedly coupled together to prevent non-destructive disassembly of the removable cartridge and may be configured to be discarded as a unit upon depletion of the liquid. A lower end of the diffusion head may be fixedly coupled to the cartridge housing in a liquid tight manner to prevent leakage from the bottom end of the removable cartridge.

The removable cartridge may further include an insert positioned above of the diffusion head, which has an inlet to receive diffused liquid generated by the venturi device, an outlet zone from which to discharge the diffused liquid toward an external environment, and a tortuous passage extending between the inlet and the outlet zone. The tortuous passage may be configured to aid in further reducing an average particle size of the diffused liquid as the diffused liquid moves through the tortuous passage. Additionally, the tortuous passage may be configured to provide a convoluted flow path that retards a flow of the liquid to be diffused through the insert when the removable cartridge is temporarily held upside-down. An initial fill level of the liquid to be diffused may be below the venturi device when the removable cartridge is upright and below a central axis of the cartridge housing when the removable cartridge is upended and rests sideways, and the tortuous passage may be configured to provide a convoluted flow path that includes a portion above the central axis when the removable cartridge is upended and rests sideways to prevent the liquid to be diffused from traversing the entirety of the tortuous passage.

A lower portion of the insert may include an indentation having an impact surface to be impinged upon by the diffused liquid generated by the venturi device during operation of the liquid diffusion device. The insert may be sandwiched between the cartridge housing and the diffusion head. The cartridge housing may include a lower housing portion and an upper housing portion, and the diffusion head and the insert may extend longitudinally between the lower housing portion and the upper housing portion.

An upper portion of the diffusion head and a lower portion of the insert may define a primary expansion chamber immediately above the venturi device. The primary expansion chamber may be in fluid communication with the internal housing cavity external of the diffusion head via a plurality of apertures provided in the upper portion of the diffusion head. The upper portion of the diffusion head may define a bulkhead that impedes the diffused liquid generated by the venturi device from exiting the primary expansion chamber other than through the plurality of apertures. An upper end of the diffusion head and the insert may be sized and shaped to nest together.

In one embodiment, the removable cartridge may consist of the cartridge housing, the diffusion head, the insert, the liquid to be diffused and a conduit that extends from a side of the venturi device of the diffusion head to a lower region of the internal housing cavity to enable the liquid contained therein to be drawn into a path of the pressurized gas as it moves through the venturi device during operation.

The removable cartridge may include a plurality of chambers downstream of the venturi device through which the diffused liquid sequentially moves towards an outlet of the removable cartridge. The plurality of chambers may include a primary expansion chamber, a secondary chamber and a tertiary chamber. The primary expansion chamber may be located immediately above the venturi device and may be bounded at least in part by a concave impact structure located opposite the venturi device. The secondary chamber may be provided above a fluid level of the liquid to be diffused and may be separated from the primary expansion chamber by a bulkhead having a plurality of apertures that provide fluid communication between the primary expansion chamber and the secondary chamber. The tertiary chamber may include a tortuous passage leading from the secondary chamber toward the outlet of the removable cartridge.

Another embodiment of a removable cartridge for use with a liquid diffusion device may be summarized be summarized as including a cartridge housing including a lower housing portion and an upper housing portion that are fixedly coupled together to prevent non-destructive disassembly of the cartridge and which collectively define an internal housing cavity that is partially filled with a liquid to be diffused, and a diffusion head retained within the internal housing cavity, which includes a venturi device for generating a diffused liquid stream. A lower portion of the diffusion head may define a gas supply conduit that extends from a bottom end of the cartridge to the venturi device to enable the venturi device to be supplied with pressurized gas from an external source via the bottom end.

DETAILED DESCRIPTION

Figure 1:
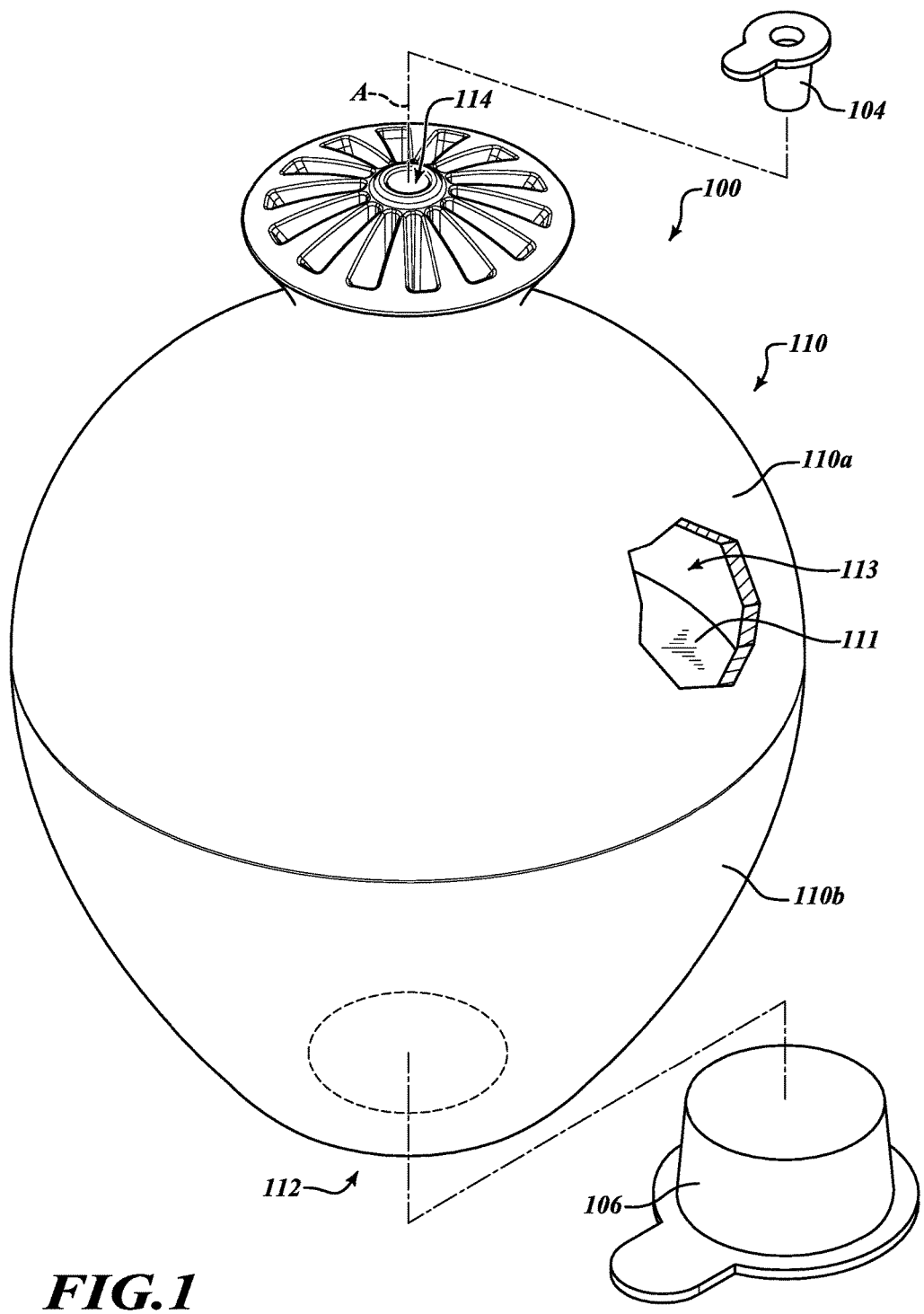
FIG. 1 is an isometric view of a removable cartridge for a liquid diffusion device, according to one embodiment.

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with liquid diffusion devices, components thereof and related methods of diffusing liquid may not be shown or described in detail to avoid unnecessarily obscuring descriptions of the embodiments. For example, embodiments of the removable cartridges and cartridge components (e.g., cartridge inserts) disclosed herein may be used in a wide variety of host diffusion devices, including those with an onboard pressurized gas source (e.g., an air compressor or pump) and a control system for discharging diffused liquid in regular or irregular duty cycles or as otherwise desired. Such diffusion devices, which may be adapted to receive embodiments of the cartridges and cartridge components described herein are not shown or described in further detail to avoid unnecessarily obscuring descriptions of such embodiments. Examples of diffusion devices and aspects and related methods thereof which may be used in combination with the cartridge and cartridge components described herein are shown in U.S. Pat. Nos. 7,712,683, 7,930,068 and 8,855,827, all of which are incorporated herein by reference in their entirety.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The present disclosure relates generally to liquid diffusion devices and more specifically to a removable cartridge 100, 200 for use with a diffusion device where the liquid to be diffused is contained within the cartridge 100, 200, and to components thereof and related methods of discharging diffused liquid into a space. The cartridges 100, 200 described herein may be used with a diffusion device or system having a unit or housing adapted to removably receive the cartridges 100, 200 such that the diffusion device or system can be recharged with liquid to be diffused. In some instances, a diffusion device may be provided which includes such a unit or housing, a removable liquid cartridge 100, 200 and a cover enclosing both the unit or housing and the cartridge 100, 200, similar to the example diffusion devices shown and described in U.S. Pat. No. 7,712,683, assigned to Prolitec, Inc., which is incorporated herein by reference in its entirety. One or more operational controls or status indicators may be provided for operating the device and an outlet or opening may be provided in the device to permit a diffused liquid generated from the liquid within the cartridge 100, 200 to be discharged into the environment about the device. When received in a host diffusion device, the removable cartridge 100, 200 engages or is otherwise coupled to an outlet of a source of pressurized gas to enable the pressurized gas to be selectively passed through the cartridge 100, 200 as described herein to diffuse the liquid contained therein. The gas used to drive the diffusion of the liquid may be any of a variety of inert gases. In some instances, the diffusion device may include an air compressor utilizing normal room air to drive the diffusion. However, other gases such as but not limited to nitrogen, carbon dioxide, or other similar atmospheric gases might be used. It may also be desirable to use a gas that reacts with the liquid to be diffused, such as but not limited to oxygen and other non-inert gases. Also, the diffusion device might utilize, for example, but be not limited to, an onboard compressor, an onboard source of compressed gas such as a pressurized reservoir, or connection to an external source of compressed gas.

Within the present disclosure, the terms atomize and diffuse are used in their various forms interchangeably. They are intended to refer to generally the same action, that being the dispersion of liquid into very small particle sizes (preferably but not limited to one micron or less in size) and releasing the particles into the atmosphere of a generally enclosed space. Discharging diffused liquid with particularly small particles helps ensure that the liquid to be dispersed remains airborne long enough to effectively treat the space.

One approach to providing small particle sizes is to incorporate a dispersion or gas-liquid mixing location adjacent an expansion chamber. The mixed gas and liquid combination may contain particles of greater than desirable size. Allowing this mix to remain resident within the expansion chamber prior to release into the treated space will allow larger particles to precipitate out of the mix. Structures that a flow of the gas and liquid mix impinge upon may also assist in the collection of these larger particles and leave only the desired predominantly smaller sized particle to be released. The expansion chamber may be maintained at a positive pressure with respect to the atmospheric pressure within the space to be treated, so that the gas and liquid mix will be injected from the device into the space. Alternatively, the expansion chamber may generally be maintained at the atmospheric pressure of the space to be treated with the flow of gas through the chamber providing the impetus for movement of the gas and liquid mix from the device into the space to be treated. It may also be possible to have the pressure within the expansion chamber at a pressure lower than that of the treated space, which may aid in the mixing or dispersion of the diffused liquid within the atmosphere within the space.

Within the context of this disclosure, diffusion also generally refers to a process or method of dispersing a liquid without destroying the integrity of the liquid compound. While some degree of reactivity between the gas and the liquid may be desirable, diffusion generally does not change the nature of the liquid, unlike heating or the application of electrical energy into the liquid to diffuse the liquid.

The removable cartridges 100, 200 and components thereof described herein may be used with a diffusion device to provide or introduce a pleasant or soothing scent (or some other type of liquid that may be used as an airborne treatment or compound) into the air space of a room or other enclosed space. The particular liquid to be dispensed by the diffusion device is contained within the removable cartridge 100, 200. Other possible types of liquids that may be dispersed may include decontamination agents, insecticides, insect repellents, and many different types of liquids that may be desirably dispersed within an enclosed space. The present disclosure is not limited to a particular type or nature of liquid to be dispersed, but is intended to encompass any desirable airborne liquid treatments that are preferably dispersed within an enclosed space to be effective. The term enclosed space, as used herein, refers to any volume of space within which the atmospheric turnover is sufficiently slow to permit the dispersed liquid to have its desired effect within the space. Larger spaces, such as concert halls, casinos, lobbies, etc., may have one or more openings into the space and still have the desired characteristics to permit treatment with a diffused liquid. Other spaces may be preferably fully enclosed to permit treatment by the selected liquid. In other cases, the liquid used for treatment may preferably be used in a sealed space for maximum effectiveness or for safety reasons. Within the scope of the present disclosure, it is not intended to limit the nature, size or configuration of the space to be treated except as may be appropriate for the liquid used to treat the space and the nature of treatment desired within the space.

A source of pressurized gas 102, 202 (FIGS. 2 and 8) may be provided within or in connection with the diffusion device that receives the removable cartridges 100, 200. The source of pressurized gas 102, 202 may comprise, for example, a small air compressor or pump, an internal reservoir, or a connection to an external source of pressurized gas. In some embodiments, controls may be configured to permit adjustment of the timing and/or pressure level of the pressurized gas or air generated by the pump or compressor that is ultimately directed into and passes through the cartridge 100, 200. In some instances, the operating pressure may be relatively low, such as, for example, less than about 2 psi gauge pressure or about 1.5 psi gauge pressure. Within the cartridge 100, 200, the pressurized gas is directed to atomize the liquid contained therein and to aid in the dispersion of the atomized liquid into the air space to be treated.

In some instances, it may be desirable to have an indirect route from the point of actual atomization of the liquid and an outlet 114, 214 (FIGS. 1 through 4 and 8) through which a portion of the atomized particles exit from the cartridge 100, 200. As will be described in greater detail below, embodiments of the removable cartridges 100, 200 described herein provide an atomization zone where liquid from the cartridge 100, 200 and pressurized gas meet and are mixed. In addition, the cartridges 100, 200 may also provide an expansion chamber or chambers within the cartridge 100, 200 where the atomized liquid is retained until a portion of the atomized liquid is allowed to exit the cartridge 100, 200 and host diffusion device. As described in greater detail elsewhere, the cartridges 100, 200 may combine storage of the liquid to be diffused, an atomization structure to transform the liquid into an airborne concentration, an expansion chamber or chambers, and a tortuous path or passage towards the outlet 114, 214 of the cartridge 100, 200. Cartridges 100, 200 according to the present disclosure may also be used in conjunction with one or more external expansion chambers to further aid in the separation of particle sizes and permit only desirably small particles to be allowed into the space to be treated.

Referring now to FIGS. 1 through 7, one example embodiment of a removable cartridge 100 is shown for use with a diffusion device which is configured to treat a space with diffused liquid generated by a flow of pressurized gas moving through the cartridge 100. As shown in FIG. 1, the removable cartridge 100 may include a housing 110 having two or more portions or pieces 110a, 110b coupled together to define a fluid receptacle having an internal cavity 113, which is partially filled with liquid 111 to be diffused. In some instances, the housing portions or pieces 110a, 110b may be fixedly coupled together to prevent non-destructive disassembly of the removable cartridge 100, making it effectively tamperproof. This may be desirable to prevent users from refilling and reusing a spent cartridge that may be ineffective or less effective in treating the space due to fouling or build-up of residue within the cartridge 100 from prior use. As an example, and with reference to FIGS. 2 through 4, the housing portion or pieces 110a, 110b, may be provided with interlocking structures 120 that snap or otherwise couple together in a manner that prevents non-destructive disassembly of the housing 110, and hence cartridge 100. A seal 122, such as an o-ring seal or other sealing device, may be provided between the housing portions or pieces 110a, 110b near the interlocking structures 120 to provide a liquid tight seal when the housing 110 is assembled. In this manner, the liquid 111 to be diffused may be prevented from leaking from the housing 110 at an interface between the housing portions or pieces 110a, 110b. Upon depletion of the liquid 111, the cartridge 100 may be readily removed and replaced with a like cartridge 100 for continued treatment of the environment surrounding the diffusion device, and the depleted cartridge 100 may be discarded as an intact unit or collected for refurbishment purposes.

With reference to FIG. 1, the housing 110 of the cartridge 100 may include an upper housing portion 110a and a lower housing portion 110b fixedly coupled together. A cartridge inlet 112 may be provided at a bottom end of the lower housing portion 110b to receive a flow of pressurized gas during operation and a cartridge outlet 114 may be provided in the upper housing portion 110a for discharging diffused liquid generated by the cartridge 100 during operation. The cartridge inlet 112 and the cartridge outlet 114 may be aligned along a central axis A defined by the housing 110. The housing 110 may be rotationally symmetric about the central axis A. For example, as shown in FIG. 1, the housing 110 may resemble an urn or similar receptacle that is rotationally symmetric about the central axis A. In other instances, the housing 110 may be asymmetrically shaped and the cartridge inlet 112 and cartridge outlet 114 may not be aligned vertically along a common axis. Respective caps or plugs 104, 106 may be provided to temporarily close the cartridge inlet 112 and cartridge outlet 114 during storage, transport or the like to prevent fouling or contamination of the cartridge 100 or possible leakage of the liquid 111 retained therein.

Internal components and structures of the cartridge 100 and related functionality will now be described with reference to FIGS. 2 through 4. According to the illustrated embodiment of the cartridge 100, the internal components and structures provide, among other things, a flow path through the cartridge 100 from the cartridge inlet 112 to the cartridge outlet 114, as represented by the arrows labeled 130a-130h. When installed in a host diffusion device, the cartridge inlet 112 is coupled a source of pressurized gas 102 such that the gas may be periodically forced through the cartridge 100 as generally represented by the arrows labeled 130a-130h to combine with the liquid 111 and to exit as a gas-liquid mixture comprising particularly small liquid particles carried by the gas, referred to generally herein as a diffused liquid.

Figure 2:
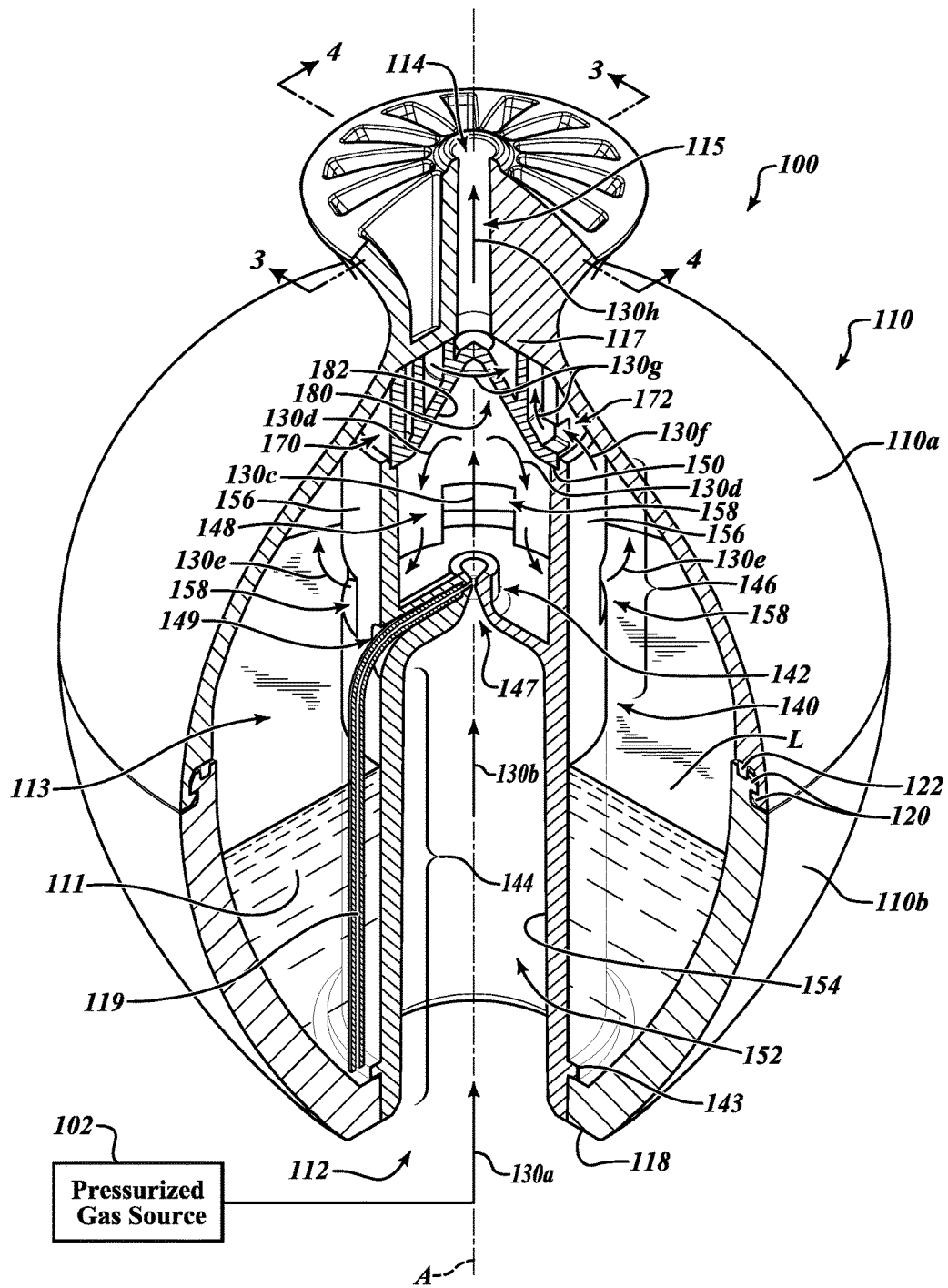
FIG. 2 is an isometric partial cross-sectional view of the removable cartridge of FIG. 1 showing internal components thereof.
Figure 3:
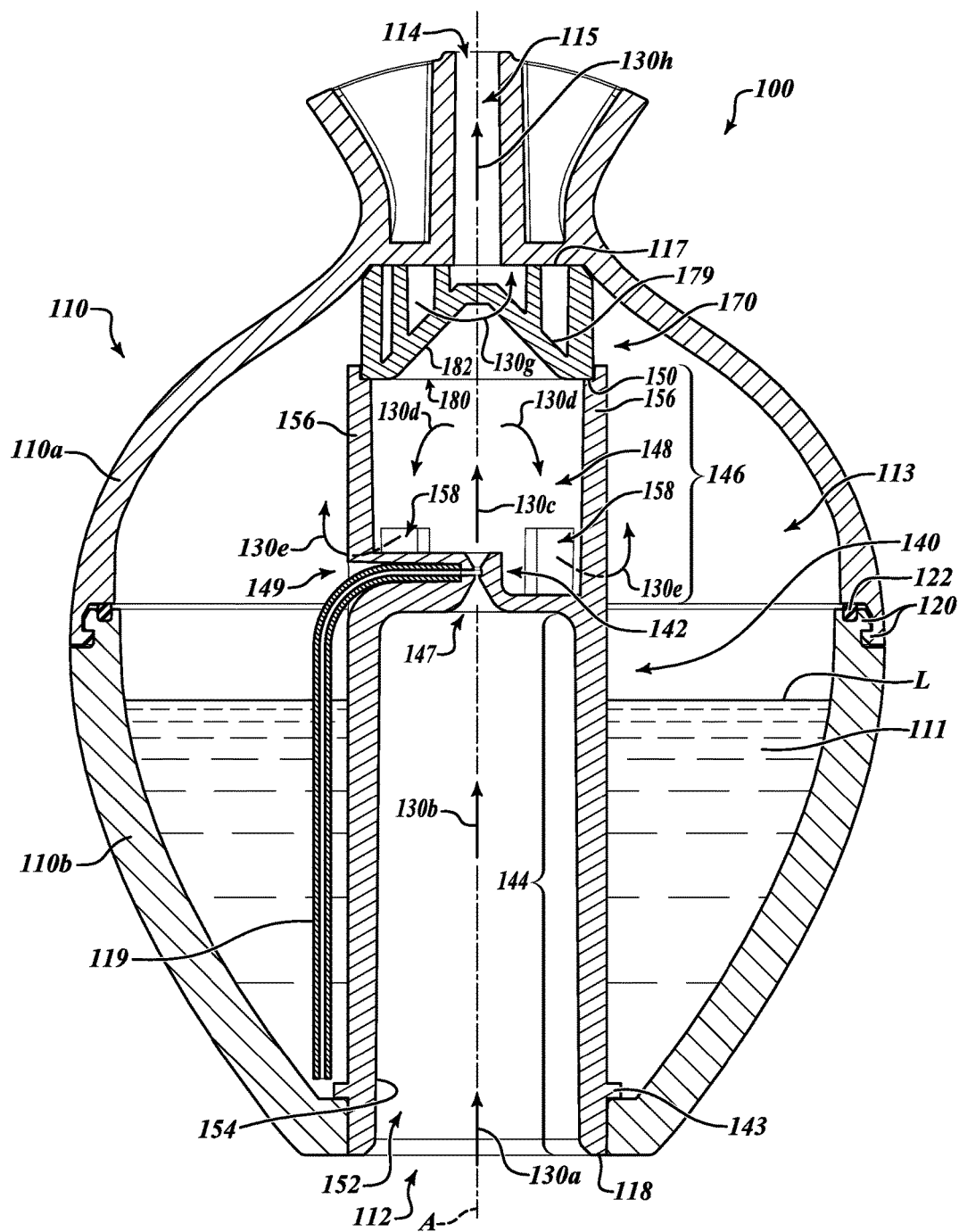
FIG. 3 is a cross-sectional view of the removable cartridge of FIG. 1 taken along line 3-3 of FIG. 2.
Figure 4:
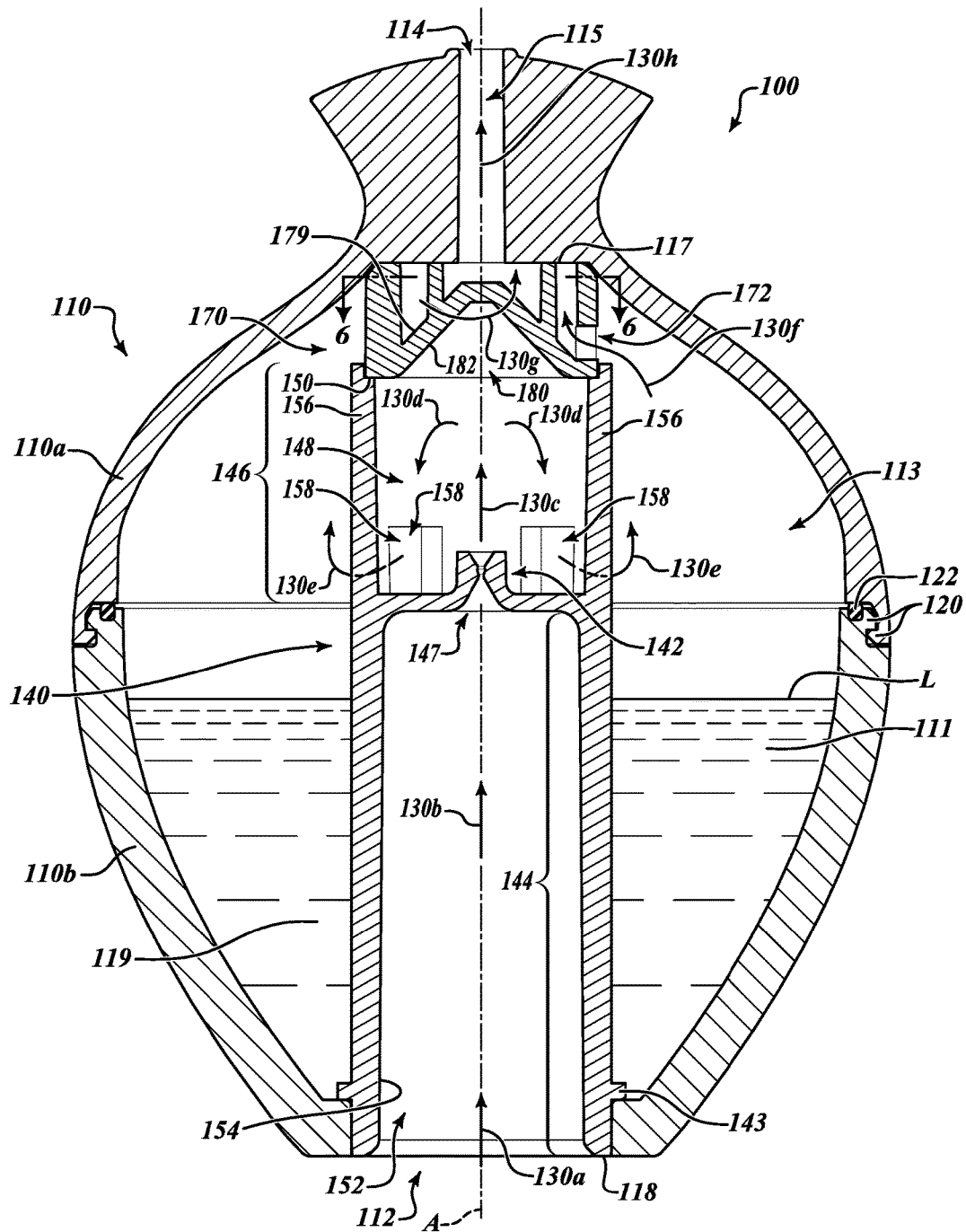
FIG. 4 is a cross-sectional view of the removable cartridge of FIG. 1 taken along line 4-4 of FIG. 2.

As shown in FIGS. 2 through 4, the pressurized gas enters the cartridge 100 through the cartridge inlet 112 at a bottom end of the housing 110 and then flows through a diffusion head 140 provided within the housing 110, which includes a venturi device 142 for drawing the retained liquid 111 into the moving gas stream, and a cartridge insert 170 before exiting the cartridge 100 through the cartridge outlet 114. More particularly, the pressurized gas enters the cartridge 100 through the cartridge inlet 112 at a bottom end of the housing 110, as represented by the arrow label 130a, and then flows upwardly through a gas supply conduit 152 defined by an interior surface 154 of a lower portion 144 of the diffusion head 140, as represented by the arrow labeled 130b. The gas then flows through the venturi device 142 drawing in liquid 111 from a fluid reservoir surrounding the lower portion 144 of the diffusion head 140 within the internal housing cavity 113 of the housing 110 to create a gas-liquid mixture comprising atomized liquid (also referred to herein as diffused liquid) that is discharged into an expansion chamber 148 provided by an upper portion 146 of the diffusion head 140, as represented by the arrow labeled 130c. The diffused liquid is then directed toward an impact structure or surface 182 located opposite the venturi device 142 wherein at least some of the diffused liquid impacts and collects on the impact structure or surface 182 and is routed back to any remaining fluid 111 in the fluid reservoir to be reintroduced into the gas stream by the venturi device 142. At least some other of the diffused liquid is redirected to flow down around bulkhead portions 156 of the diffusion head 140 and to pass through passageways 158 in the diffusion head 140 leading to a portion of the internal cavity 113 of the housing above the fluid level L of liquid 111 in the cartridge 100, as represented by the arrows labeled 130d and 130e. From there, some of the diffused liquid may collect on the exposed interior surfaces of the housing 110 or other internal structures of the cartridge 100, or otherwise precipitate out of the gas and atomized liquid, and rejoin the liquid 111 in the fluid reservoir to be reintroduced into the gas stream by the venturi device 142. Some other of the diffused liquid may be propelled into the cartridge insert 170 via an inlet 172 thereof, as represented by the arrow labeled 130f. From the inlet 172 of the insert 170, the diffused liquid proceeds along a tortuous passage through the cartridge insert 170, as represented by the arrows labeled 130g, before passing through an outlet passageway 115 in the housing 110 that leads to the cartridge outlet 114 to be discharged from the cartridge 100, as represented by the arrow labeled 130h. In making this convoluted journey from the expansion chamber 148 to the cartridge outlet 114, the liquid particle size distribution of the diffused liquid is refined such that only particularly fine particles are successfully discharged from the cartridge 100 with relatively larger particles collecting on one or more surfaces of the internal structures and components of the cartridge 100, or otherwise precipitating out of the gas, for rejoinder with remaining liquid 111 in the liquid reservoir for reintroduction into the gas stream passing through the venturi device 142.

Figures 5, 6:
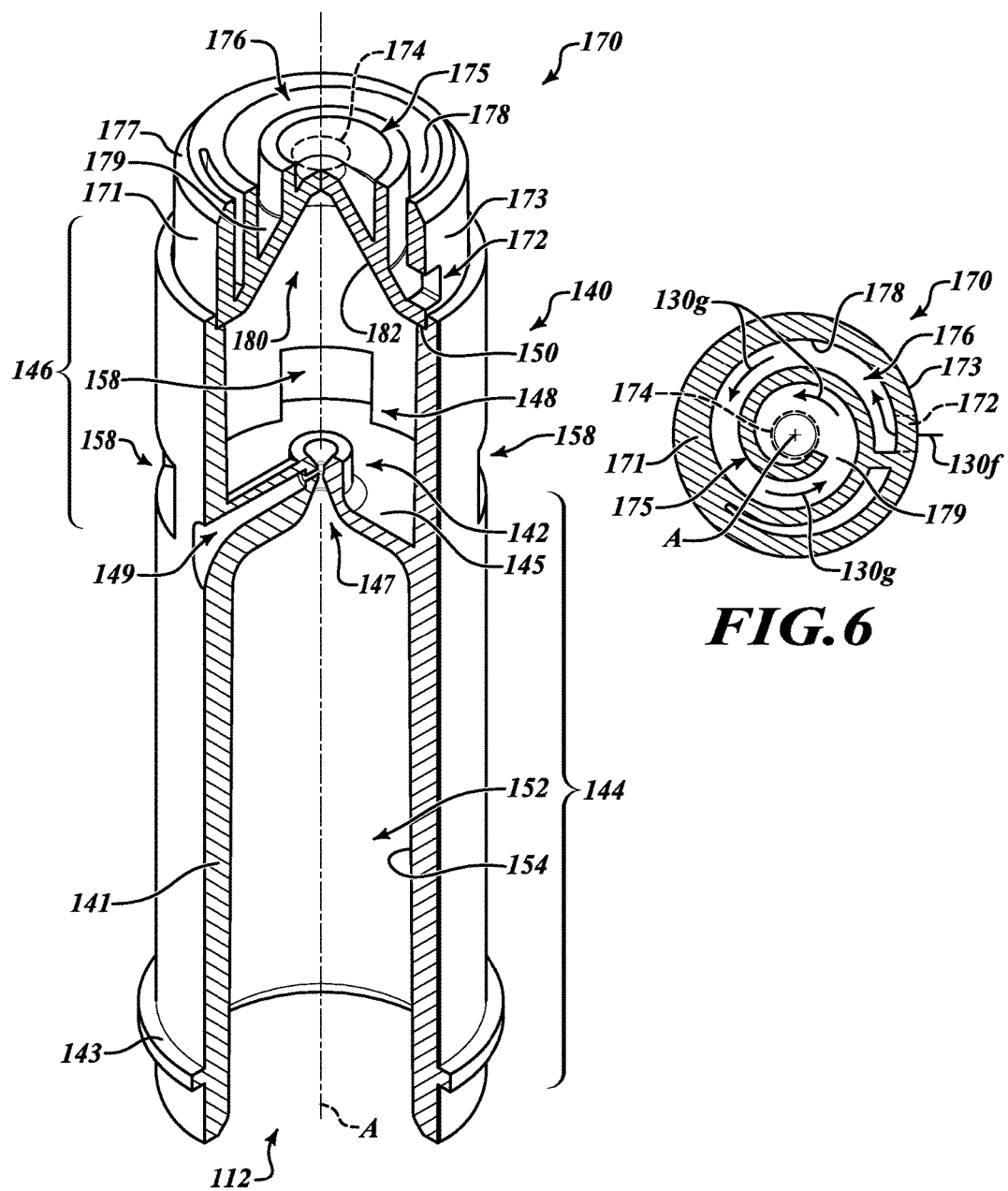
FIG. 5 is an isometric partial cross-sectional view of a diffusion head and an insert of the removable cartridge of FIG. 1.
FIG. 6 is a cross-sectional view of the insert of the removable cartridge of FIG. 1 taken along line 6-6 of FIG. 4 showing a flow path for diffused liquid moving therethrough.

Further details of the diffusion head 140 and cartridge insert 170 will now be discussed with reference to FIG. 5. As shown in FIG. 5, the diffusion head 140 may include a unitary diffusion head body 141 including an upstream or lower portion 144 and a downstream or upper portion 146. For example, in some instances the diffusion head 140 may be molded or otherwise formed as a unitary piece of material, such as a suitable plastic or polymeric material. The lower portion 144 of the diffusion head 140 may be sized and shaped to nest closely with a corresponding portion of the housing 110, as shown in FIGS. 1 through 4, or to otherwise interface with the housing 110, and may be fixedly joined to the housing 110 via spin welding, ultrasonic welding other joining processes to create a liquid-tight seal between the housing 110 and the lower portion 144 of the diffusion head 140. In some instances, such as the example embodiment of the diffusion head 140 shown in FIG. 5, the lower portion 144 of the diffusion head body 141 may include a flange 143 or other feature, such as a step, projection, tab, indent, or groove, that interfaces with the housing 110 to assist in fitment and joining of the components.

With continued reference to FIG. 5, the lower portion 144 of the diffusion head body 141 includes an interior surface 154 that defines the gas supply conduit 152 that leads from the cartridge inlet 112 at a bottom end of the cartridge 100 toward the venturi device 142. The gas supply conduit 152 may also be partially defined by a divider portion 145 of the diffusion head body 141 which divides the upper portion 146 of the diffusion head 140 from the lower portion 144. The divider portion 145 separates and isolates the gas supply conduit 152 from the expansion chamber 148 with the exception of a flow passage 147 through the venturi device 142 which may provide the only fluid communication between the gas supply conduit 152 and the expansion chamber 148.

With reference to FIGS. 2 and 3, the liquid 111 to be diffused may surround the lower portion 144 of the diffusion head 140 such that gas enters the cartridge 100 from a bottom 118 of the cartridge 100 and passes through a region of the diffusion head 140 surrounded by the liquid 111 before reaching the venturi device 142. At the venturi device 142, the gas is accelerated via the flow passage 147 and a lower pressure zone is created which draws the liquid 111 to be diffused through a suction tube 119 that provides fluid communication between the liquid reservoir that surrounds the lower portion 144 of the diffusion head 140 and the venturi device 142. The initial volume of liquid 111 supplied with the cartridge 100 preferably does not fill the entire interior cavity 113 of the housing 110, but rather defines a fluid level L that is below the venturi device 142.

As shown in FIG. 5, the diffusion head 140 may include a tube receiving passage 149 in the divider portion 145 of the diffusion head body 141 to receive one end of the suction tube 119 and to position an outlet of the suction tube 119 in fluid communication with the flow passage 147 of the venturi device 142 such that the liquid 111 may be drawn into the path of the pressurized gas as it is accelerated via the flow passage 147 of the venturi device 142. The flow passage 147 of the venturi device 142 may comprise a convergent entrance, a narrow throat, a side port for introduction of the liquid, and a divergent outlet which are configured to accelerate the flow of gas, draw in the liquid 111 through the side port and discharge diffused liquid into the downstream expansion chamber 148 provided by the upper portion 146 of the diffuser head 140. The size and shape of the flow passage 147 may be configured based on characteristics of the gas flow, the geometry of the gas supply conduit 152 and the volume and velocity of gas required to effectively draw liquid 111 up the suction tube 119 and atomize liquid 111 in the venturi device 142.

With continued reference to FIG. 5, the diffused liquid may be discharged from the venturi device 142 with sufficient force to cause at least some of the atomized liquid particles suspended in the gas, particularly the relatively larger particles, to impinge upon and collect on the underside of the cartridge insert 170, which is provided opposite the venturi device 142 to serve as an impact structure, preferably a concave impact structure. More particularly, the insert 170 may include a lower portion having an indentation or depression 180 that includes an impact surface 182 to be impinged upon by the diffused liquid generated by the venturi device 142 during operation. In some instances, the impact surface 182 may be concave and may diverge in a downward direction to direct liquid condensed or collected thereon radially outward and downward. In some embodiments, the impact surface 182 may be a conical or frustoconical surface. Liquid collecting on the underside of the insert 170 may drip or run down onto the divider portion 145 of the diffusion head 140 and drain to the liquid reservoir via the passageways 158 provided in the upper portion 146 of the diffusion head 140, which in some embodiments may provide the only fluid communication between the expansion chamber 148 and the internal cavity 113 of the housing 110 external of the diffusion head 140.

As shown in FIG. 5, the insert 170 is positioned above of the diffusion head 140 and includes a body 171, an inlet 172 provided in the body 171 to receive the diffused liquid generated within the cartridge 100 during operation of the liquid diffusion device, an outlet zone 174 defined at least in part by the body 171 through which to discharge the diffused liquid toward the external environment, and a tortuous passage 176 extending between the inlet 172 and the outlet zone 174 to aid in further reducing an average liquid particle size of the diffused liquid as the diffused liquid moves through the tortuous passage 176 during operation. The inlet 172 may be located at a periphery 173 of the body 171, the outlet zone 174 may be located at a central region 175 of the body 171, and the tortuous passage 176 may spiral or otherwise extend in a convoluted manner between the inlet 172 and the outlet zone 174. The tortuous passage 176 may be at least partially defined by a vertical sidewall 178 of the body 171. The sidewall 178 may extend from the periphery 173 of the body 171 into the central region 175 of the body 171. A floor 179 of the insert 170 may be inclined or sloped toward the inlet 172 to assist in rerouting liquid that has precipitated out of the gas/diffused liquid mixture or that has otherwise collected on surfaces of the insert 170 as the mixture passes through the tortuous passage 176 during operation back to rejoin any remaining liquid 111 in the internal cavity 113 surrounding the lower portion 144 of the diffusion head 140 to be reintroduced into the gas stream passing through the venturi device 142.

As shown in FIG. 5, the tortuous passage 176 may be open in an upward direction and may be at least partially capped with a corresponding portion 117 of the housing 110 when the cartridge 100 is assembled to define an aerosol outlet at a remaining uncovered portion at the outlet zone 174. The insert 170 may also include a chamfer 177 of other feature or structure for interfacing with the housing 110 to assist in alignment and fitment of the insert 170 within the cartridge 100 as the insert 170 is sandwiched between the cartridge housing 110 and the diffusion head 140 in the assembled condition. In the assembled condition, the diffusion head 140 and the insert 170 extend longitudinally between the lower housing portion 110b and the upper housing portion 110a to define a central core of the cartridge 100 that fully traverses the housing 110 in a longitudinal direction.

The body 171 of the insert 170 is preferably formed as a single, unitary piece that includes the tortuous passage 176 and is coupled to or otherwise positioned adjacent the upper portion 146 of the diffusion head 140 to cap the expansion chamber 148. For example, in some instances the insert 170 may be molded or otherwise formed as a unitary piece of material, such as a suitable plastic or polymeric material. The upper portion 146 of the diffusion head 140 and the insert 170 may be sized and shaped to nest together. For example, the upper portion 146 of the diffusion head 140 may include a recess or shelf 150 to receive and support the insert 170. In some embodiments, the insert 170 may be fixedly joined to the diffusion head 140 via spin welding, ultrasonic welding or other joining techniques. Still further, although the diffusion head 140 and the insert 170 are described herein as two separate components positioned or joined together, it is appreciated that the structures and features of these components may be formed as a single unitary piece via an additive manufacturing process, for example. In other instances, the structures and features of the diffusion head 140 and the insert 170 may be provided by more than two pieces that are joined or otherwise coupled together. In the particularly advantageous embodiment illustrated in FIGS. 1 through 7, however, the removable cartridge 100 consists of, or consists essentially of, the cartridge housing 110, the diffusion head 140, the cartridge insert 170, the liquid 111 to be diffused, and the conduit or tube 119 that extends from a side of the venturi device 142 of the diffusion head 140 to a lower region of the internal housing cavity 113 to enable the liquid 111 contained therein to be drawn into the path of the pressurized gas as it moves through the venturi device 142 during operation.

According to the illustrated embodiment, the tortuous passage 176 is helical and makes at least one full revolution about the central axis A. It is appreciated, however, that the tortuous passage 176 may take on a variety of different forms. For example, the tortuous passage 176 may include a curvilinear path that at least partially encircles the central axis A as it moves from the inlet 172 toward the outlet zone 174. In other instances, the tortuous passage 176 may include a path with a plurality of straight segments angled relative to each other to provide a number of turns. In still other instances, the tortuous passage 176 may include a path that combines linear and non-linear path segments. The cross-sectional shape of the tortuous passage 176 may also vary along the tortuous passage 176. For example, a cross-sectional profile of at least a portion of the tortuous passage 176 may narrow in a downstream direction, that is in a direction from the inlet 172 toward the outlet zone 174. This narrowing of the tortuous passage 176 may further assist in refining the composition of the diffused liquid to include only the finest of liquid particles.

Figure 7:
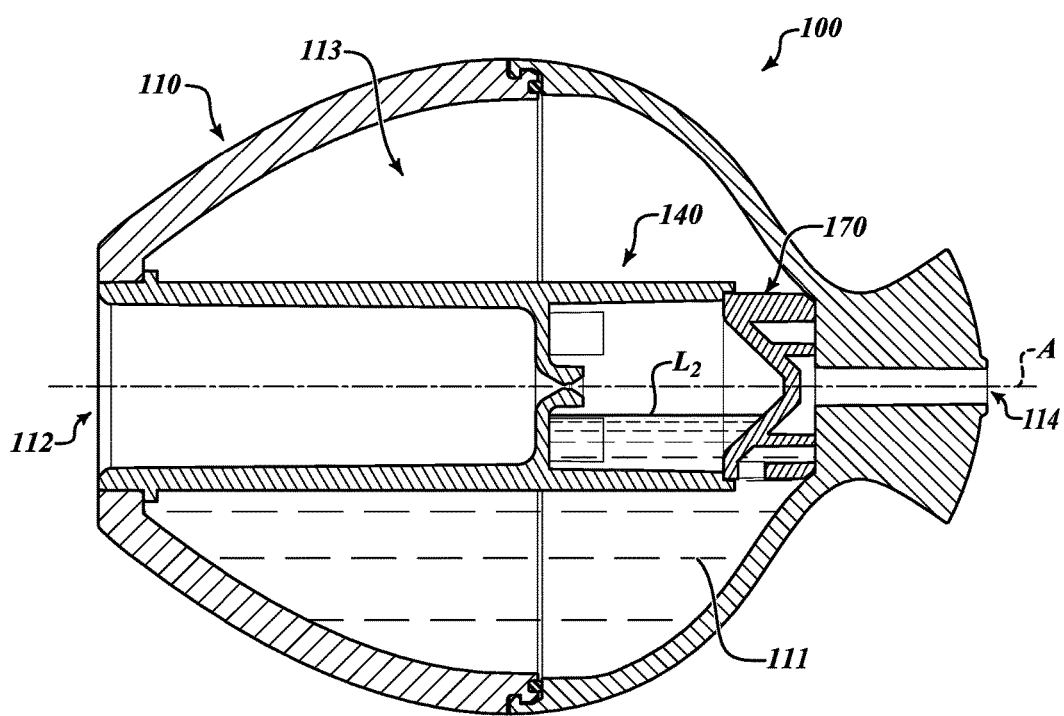
FIG. 7 is a cross-sectional view of the removable cartridge of FIG. 1 taken along line 4-4 of FIG. 2, but rotated on its side.

Irrespective of particular configuration, the tortuous passage 176 follows a non-linear path that, among other things, assists in preventing liquid 111 from leaking from the cartridge 100 when the cartridge 100 is upended. For example, if the cartridge 100 is temporarily held upside down, the tortuous passage 176 will assist in slowing the progression of liquid 111 within the cartridge 100 toward the outlet zone 174 and hence the outlet 114 of the cartridge 100. In this manner, the cartridge 100 can be subsequently righted without the loss of fluid. Moreover, in the event the cartridge 100 is upended and comes to rest on its side, the cartridge 100 is configured such that the volume of liquid 111 supplied with the cartridge 100 will not rise above the central axis A of the cartridge 100, as illustrated in FIG. 7. In this manner, the tortuous passage 176 will prevent the liquid 111 from spilling out of the outlet 114 as the liquid 111 will be unable to move through the entirety of the tortuous passage 176 as at least a portion of the tortuous passage 176 will be located above the fluid level $L_2$ of the liquid 111.

Figure 8:
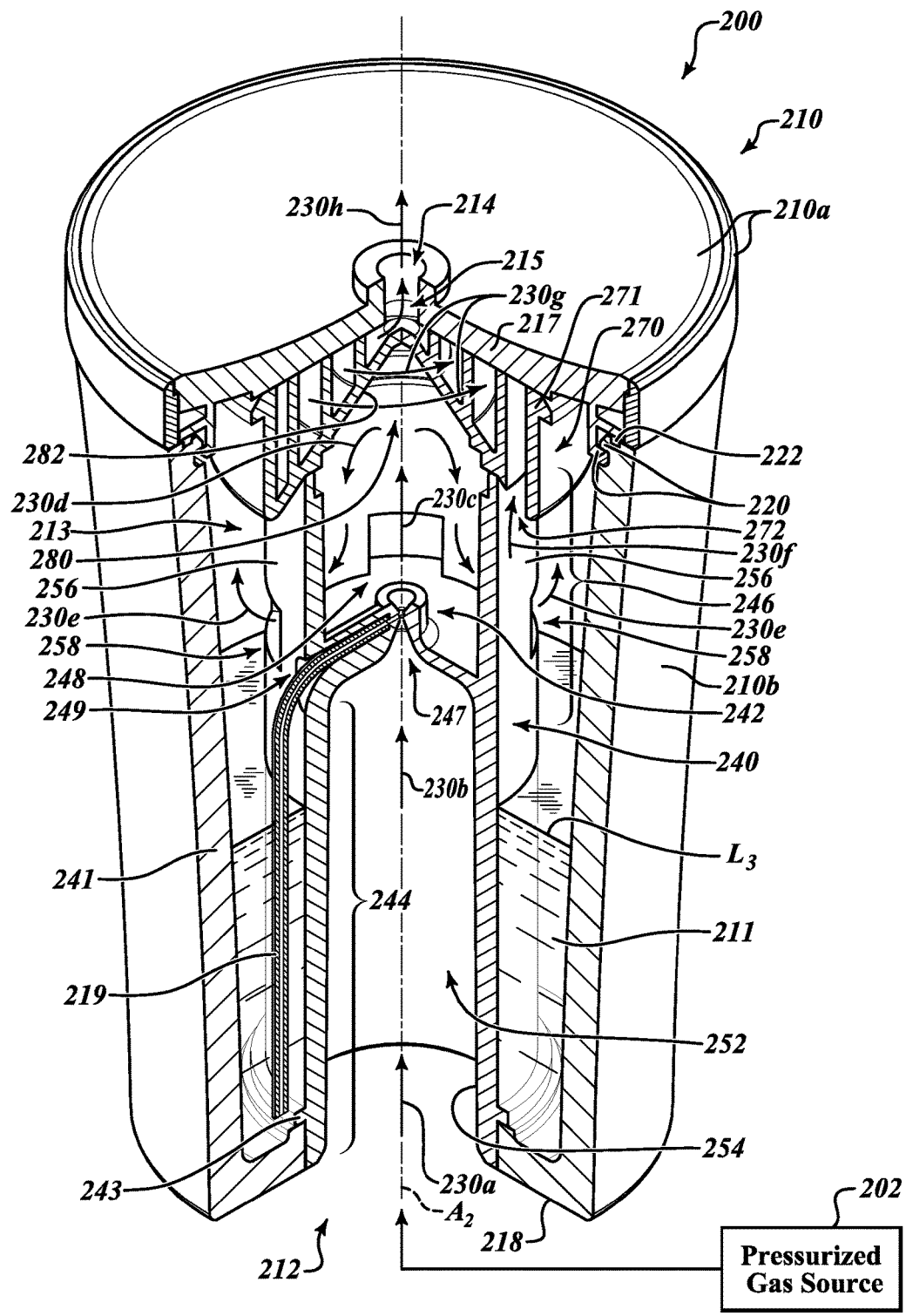
FIG. 8 is an isometric partial cross-sectional view of a removable cartridge for a liquid diffusion device, according to another embodiment.

With reference again to FIGS. 2 through 4, it will be appreciated that the housing 110 and internal components of the cartridge 100 define a plurality of distinct chambers downstream of the venturi device 142 through which the diffused liquid sequentially travels before being discharged from the cartridge 100 and ultimately into a surrounding environment. More particularly, the upper portion 146 of the diffusion head 140 and a lower portion of the insert 170 define a primary expansion chamber 148 immediately above the venturi device 142, a secondary chamber is provided external of the diffusion head 140 and the insert 170 within internal cavity 113 of the housing 110 above the fluid level L of the liquid 111 to be diffused, and a tertiary chamber is provided by the tortuous passage 176 of the insert 170. Passageways or apertures 158 in the upper portion 146 of the diffusion head 140 provide fluid communication between the primary expansion chamber 148 and the secondary chamber. The upper portion 146 of the diffusion head 140 also defines a bulkhead or bulkhead portions 156 that impede the diffused liquid generated by the venturi device 142 from exiting the primary expansion chamber 148 other than through the plurality of passageways or apertures 158. The inlet 172 of the insert 170 provides fluid communication between the secondary chamber and the tertiary chamber (i.e., the tortuous passage 176). Although only one inlet 172 and one tortuous passage 176 is shown providing the sole passage for the diffused liquid to exit the cartridge 100, it is appreciated that a plurality of inlets 172 may be provide to enable diffused liquid to enter one or more tortuous passages leading to the outlet 114 of the cartridge 100. The distinct chambers described above (i.e., the primary expansion chamber, the secondary chamber and the tertiary chamber) collectively assist in refining the composition of the diffused liquid to include only the finest liquid particles as the diffused liquid moves sequentially through the chambers during operation. For instance, by the time the gas/diffused liquid mixture exits from cartridge 100, there has been some residence time in each of the distinct chambers to permit undesirably large liquid particles or droplets to precipitate out of or otherwise separate from the mixture and be returned to the liquid reservoir within the internal cavity 113 of the housing 110 external of the diffusion head 140 for later atomization and dispersion. In this manner, the removable cartridge 100 and components thereof may provide a cartridge solution for a diffusion device which has an efficient form factor that is particularly effective at treating spaces with diffused liquid having extremely small liquid particles.

Referring now to FIGS. 8 through 10, another example embodiment of a removable cartridge 200 is shown for use with a diffusion device which is configured to treat a space with diffused liquid generated by a flow of pressurized gas moving through the cartridge 200. As shown in FIG. 8, the removable cartridge 200 may include a housing 210 having two or more portions or pieces 210*a*, 210*b* coupled together to define, among other things, a fluid receptacle having an internal cavity 213 partially filled with liquid 211 to be diffused. In some instances, the housing portions or pieces 210*a*, 210*b* may be fixedly coupled together to prevent non-destructive disassembly of the removable cartridge 200, making it effectively tamperproof. This may be desirable to prevent users from refilling and reusing a spent cartridge that may be ineffective or less effective in treating the space due to fouling or build-up of residue within the cartridge 200 from prior use. As an example, and with reference to FIG. 8, the housing portion or pieces 210*a*, 210*b*, may be provided with interlocking structures 220 that snap or otherwise couple together in a manner that prevents non-destructive disassembly of the housing 210, and hence cartridge 200. A seal 222, such as an o-ring seal or other sealing device, may be provided between the housing portions or pieces 210*a*, 210*b* near the interlocking structures 220 to provide a liquid tight seal when the housing 210 is assembled. In this manner, the liquid 211 to be diffused may be prevented from leaking from the housing 210 at an interface between the housing portions or pieces 210*a*, 210*b*. Upon depletion of the liquid 211, the cartridge 200 may be readily removed and replaced with a like cartridge 200 for continued treatment of the environment surrounding the diffusion device, and the depleted cartridge 200 may be discarded as an intact unit or collected for refurbishment purposes.

With reference to FIG. 8, the housing 210 of the cartridge 200 may include an upper housing portion 210*a* and a lower housing portion 210*b* fixedly coupled together. A cartridge inlet 212 may be provided at a bottom end of the lower housing portion 210*b* to receive a flow of pressurized gas during operation and a cartridge outlet 214 may be provided in the upper housing portion 210*a* for discharging diffused liquid generated by the cartridge 200 during operation. The cartridge inlet 212 and the cartridge outlet 214 may be aligned along a central axis $A_2$ defined by the housing 210. The housing 210 may be rotationally symmetric about the central axis $A_2$. For example, as shown in FIG. 8, the housing 210 may resemble a generally cylindrical vessel or similar receptacle that is rotationally symmetric about the central axis $A_2$. In other instances, the housing 210 may be asymmetrically shaped and the cartridge inlet 212 and cartridge outlet 214 may not be aligned vertically along a common axis. Respective caps or plugs (not shown) may be provided to temporarily close the cartridge inlet 212 and cartridge outlet 214 during storage, transport or the like to prevent fouling or contamination of the cartridge 200 or possible leakage of the liquid 211 retained therein.

Internal components and structures of the cartridge 200 and related functionality will now be described with reference to FIG. 8. According to the illustrated embodiment of the cartridge 200, the internal components and structures provide, among other things, a flow path through the cartridge 200 from the cartridge inlet 212 to the cartridge outlet 214, as represented by the arrows labeled 230*a*-230*h*. When installed in a host diffusion device, the cartridge inlet 212 is coupled a source of pressurized gas 202 such that the gas may be periodically forced through the cartridge 200 as generally represented by the arrows labeled 230*a*-230*h* to combine with the liquid 211 and to exit as a gas-liquid mixture comprising particularly small liquid particles carried by the gas, referred to generally herein as a diffused liquid.

As shown in FIG. 8, the pressurized gas enters the cartridge 200 through the cartridge inlet 212 at a bottom end of the housing 210 and then flows through a diffusion head 240 provided within the housing 210, which includes a venturi device 242 for drawing the retained liquid 211 into the moving gas stream, and a cartridge insert 270 before exiting the cartridge 200 through the cartridge outlet 214. More particularly, the pressurized gas enters the cartridge 200 through the cartridge inlet 212 at a bottom end of the housing 210, as represented by the arrow label 230*a*, and then flows upwardly through a gas supply conduit 252 defined by an interior surface 254 of a lower portion 244 of the diffusion head 240, as represented by the arrow labeled 230*b*. The gas then flows through the venturi device 242 drawing in liquid 211 from a fluid reservoir surrounding the lower portion 244 of the diffusion head 240 within the internal housing cavity 213 of the housing 210 to create a gas-liquid mixture comprising atomized liquid (also referred to herein as diffused liquid) that is discharged into an expansion chamber 248 provided by an upper portion 246 of the diffusion head 240, as represented by the arrow labeled 230*c*. The diffused liquid is then directed toward an impact structure or surface 282 located opposite the venturi device 242 wherein at least some of the diffused liquid impacts and collects on the impact structure or surface 282 and is routed back to any remaining fluid 211 in the fluid reservoir to be reintroduced into the gas stream by the venturi device 242. At least some other of the diffused liquid is redirected to flow down around bulkhead portions 256 of the diffusion head 240 and to pass through passageways 258 in the diffusion head 240 leading to a portion of the internal cavity 213 of the housing above the fluid level $L_3$ of liquid 211 in the cartridge 200, as represented by the arrows labeled 230*d* and 230*e*. From there, some of the diffused liquid may collect on the exposed interior surfaces of the housing 210 or other internal structures of the cartridge 200, or otherwise precipitate out of the gas and atomized liquid, and rejoin the liquid 211 in the fluid reservoir to be reintroduced into the gas stream by the venturi device 242. Some other of the diffused liquid may be propelled into the cartridge insert 270 via an inlet 272 thereof, as represented by the arrow labeled 230*f*. From the inlet 272 of the insert 270, the diffused liquid proceeds along a tortuous passage 276 (see FIGS. 9 and 10) through the cartridge insert 270, as represented by the arrows labeled 230*g*, before passing through an outlet passageway 215 in the housing 210 that leads to the cartridge outlet 214 to be discharged from the cartridge 200, as represented by the arrow labeled 230*h*. In making this convoluted journey from the expansion chamber 248 to the cartridge outlet 214, the liquid particle size distribution of the diffused liquid is refined such that only particularly fine particles are successfully discharged from the cartridge 200 with relatively larger particles collecting on one or more surfaces of the internal structures and components of the cartridge 200, or otherwise precipitating out of the gas, for rejoinder with remaining liquid 211 in the liquid reservoir for reintroduction into the gas stream passing through the venturi device 242.

As shown in FIG. 8, the diffusion head 240 may include a unitary diffusion head body 241 including an upstream or lower portion 244 and a downstream or upper portion 246. For example, in some instances the diffusion head 240 may be molded or otherwise formed as a unitary piece of material, such as a suitable plastic or polymeric material. The lower portion 244 of the diffusion head 240 may be sized and shaped to nest closely with a corresponding portion of the housing 210, as shown in FIG. 8, or to otherwise interface with the housing 210, and may be fixedly joined to the housing 210 via spin welding, ultrasonic welding other joining processes to create a liquid-tight seal between the housing 210 and the lower portion 244 of the diffusion head 240. In some instances, such as the example embodiment of the diffusion head 240 shown in FIG. 8, the lower portion 244 of the diffusion head body 241 may include a flange 243 or other feature, such as a step, projection, tab, indent, or groove, that interfaces with the housing 210 to assist in fitment and joining of the components.

With continued reference to FIG. 8, the lower portion 244 of the diffusion head body 241 includes an interior surface 254 that defines the gas supply conduit 252 that leads from the cartridge inlet 212 at a bottom end of the cartridge 200 toward the venturi device 242. The gas supply conduit 252 may also be partially defined by a divider portion 245 of the diffusion head body 241 which divides the upper portion 246 of the diffusion head 240 from the lower portion 244. The divider portion 245 separates and isolates the gas supply conduit 252 from the expansion chamber 248 with the exception of a flow passage 247 through the venturi device 242 which provides the only fluid communication between the gas supply conduit 252 and the expansion chamber 248.

With continued reference to FIG. 8, the liquid 211 to be diffused may surround the lower portion 244 of the diffusion head 240 such that gas enters the cartridge 200 from a bottom 218 of the cartridge 200 and passes through a region of the diffusion head 240 surrounded by the liquid 211 before reaching the venturi device 242. At the venturi device 242, the gas is accelerated via the flow passage 247 and a lower pressure zone is created which draws the liquid 211 to be diffused through a suction tube 219 that provides fluid communication between the liquid reservoir that surrounds the lower portion 244 of the diffusion head 240 and the venturi device 242. The initial volume of liquid 211 supplied with the cartridge 200 preferably does not fill the entire interior cavity 213 of the housing 210, but rather defines a fluid level $L_3$ that is below the venturi device 242.

As shown in FIG. 8, the diffusion head 240 may include a tube receiving passage 249 in the divider portion 245 of the diffusion head body 241 to receive one end of the suction tube 219 and to position an outlet of the suction tube 219 in fluid communication with the flow passage 247 of the venturi device 242 such that the liquid 211 may be drawn into the path of the pressurized gas as it is accelerated via the flow passage 247 of the venturi device 242. The flow passage 247 of the venturi device 242 may comprise a convergent entrance, a narrow throat, a side port for introduction of the liquid, and a divergent outlet which are configured to accelerate the flow of gas, draw in the liquid 211 through the side port and discharge diffused liquid into the downstream expansion chamber 248 provided by the upper portion 246 of the diffuser head 240. The size and shape of the flow passage 247 may be configured based on characteristics of the gas flow, the geometry of the gas supply conduit 252 and the volume and velocity of gas required to effectively draw liquid 211 up the suction tube 219 and atomize liquid 211 in the venturi device 242.

With continued reference to FIG. 8, the diffused liquid may be discharged from the venturi device 242 with sufficient force to cause at least some of the atomized liquid particles suspended in the gas, particularly the relatively larger particles, to impinge upon and collect on the underside of the cartridge insert 270, which is provided opposite the venturi device 242 to serve as an impact structure, preferably a concave impact structure. More particularly, the insert 270 may include a lower portion having an indentation or depression 280 that includes an impact surface 282 to be impinged upon by the diffused liquid generated by the venturi device 242 during operation. In some instances, the impact surface 282 may be concave and may diverge in a downward direction to direct liquid condensed or collected thereon radially outward and downward. In some embodiments, the impact surface 282 may be a conical or frustoconical surface. Liquid collecting on the underside of the insert 270 may drip or run down onto the divider portion 245 of the diffusion head 240 and drain to the liquid reservoir via the passageways 258 provided in the upper portion 246 of the diffusion head 240, which in some embodiments may provide the only fluid communication between the expansion chamber 248 and the internal cavity 213 of the housing 210 external of the diffusion head 240.

Figure 9:
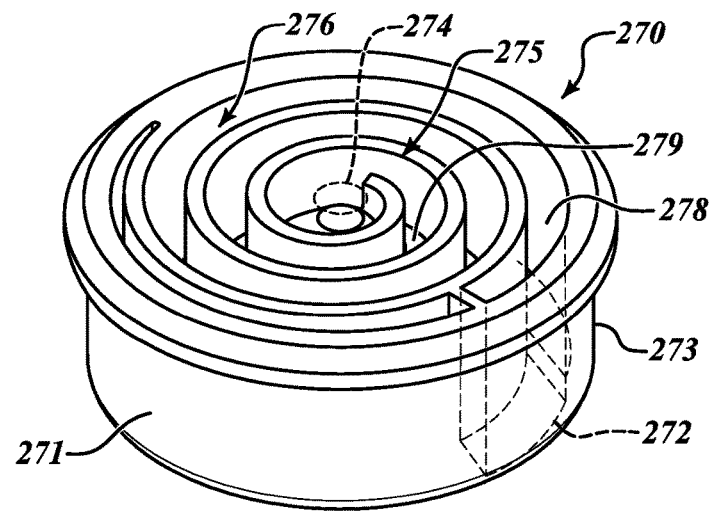
FIG. 9 is an isometric view of an insert of the removable cartridge of FIG. 8.
Figure 10:
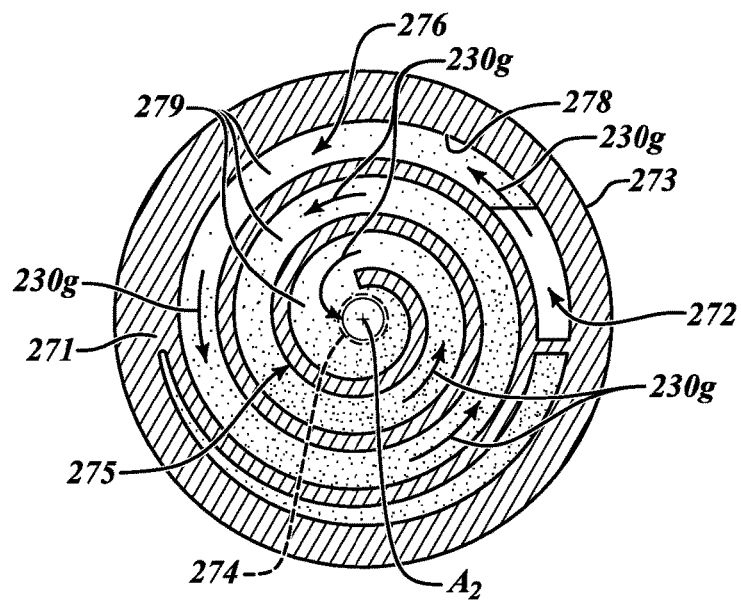
FIG. 10 is a cross-sectional view of the insert shown in FIG. 9 showing a flow path for diffused liquid moving therethrough.

With reference to FIGS. 8 through 10, the insert 270 is positioned above of the diffusion head 240 and includes a body 271, an inlet 272 provided in the body 271 to receive the diffused liquid generated within the cartridge 200 during operation of the liquid diffusion device, an outlet zone 274 defined at least in part by the body 271 through which to discharge the diffused liquid toward the external environment, and a tortuous passage 276 extending between the inlet 272 and the outlet zone 274 to aid in further reducing an average liquid particle size of the diffused liquid as the diffused liquid moves through the tortuous passage 276 during operation. The inlet 272 may be located at or near a periphery 273 of the body 271, the outlet zone 274 may be located at a central region 275 of the body 271, and the tortuous passage 276 may spiral or otherwise extend in a convoluted manner between the inlet 272 and the outlet zone 274. The tortuous passage 276 may be at least partially defined by a vertical sidewall 278 of the body 271. The sidewall 278 may extend from the periphery 273 of the body 271 into or towards the central region 275 of the body 271. A floor 279 of the insert 270 may be inclined or sloped toward the inlet 272 to assist in rerouting liquid that has precipitated out of the gas/diffused liquid mixture or that has otherwise collected on surfaces of the insert 270 as the mixture passes through the tortuous passage 276 during operation back to rejoin any remaining liquid 211 in the internal cavity 213 surrounding the lower portion 244 of the diffusion head 240 to be reintroduced into the gas stream passing through the venturi device 242.

As shown in FIGS. 8 and 9, the tortuous passage 276 may be open in an upward direction and may be at least partially capped with a corresponding portion 217 of the housing 210 when the cartridge 200 is fully assembled to define an aerosol outlet at a remaining uncovered portion at the outlet zone 274. The insert 270 may be sandwiched between the cartridge housing 210 and the diffusion head 240 in the assembled condition. In the assembled condition, the diffusion head 240 and the insert 270 extend longitudinally between the lower housing portion 210b and the upper housing portion 210a to define a central core of the cartridge 200 that fully traverses the housing 210 in a longitudinal direction.

The body 271 of the insert 270 is preferably formed as a single, unitary piece that includes the tortuous passage 276 and is coupled to or otherwise positioned adjacent the upper portion 246 of the diffusion head 240 to cap the expansion chamber 248. For example, in some instances the insert 270 may be molded or otherwise formed as a unitary piece of material, such as a suitable plastic or polymeric material. The upper portion 246 of the diffusion head 240 and the insert 270 may be sized and shaped to nest together. For example, the upper portion 246 of the diffusion head 240 may include a recess or shelf to receive and support the insert 270. In other instances, the upper portion 246 of the diffusion head 240 and the insert 270 may abut each other along planar surfaces. In some embodiments, the insert 270 may be fixedly joined to the diffusion head 240 via spin welding, ultrasonic welding or other joining techniques. Still further, although the diffusion head 240 and the insert 270 are described herein as two separate components positioned or joined together, it is appreciated that the structures and features of these components may be formed as a single unitary piece via an additive manufacturing process, for example. In other instances, the structures and features of the diffusion head 240 and the insert 270 may be provided by more than two pieces that are joined or otherwise coupled together. In the particularly advantageous embodiment illustrated in FIGS. 8 through 10, however, the removable cartridge 200 consists, or consists essentially, of the cartridge housing 210, the diffusion head 240, the cartridge insert 270, the liquid 211 to be diffused, and the conduit or tube 219 that extends from a side of the venturi device 242 of the diffusion head 240 to a lower region of the internal housing cavity 213 to enable the liquid 211 contained therein to be drawn into the path of the pressurized gas as it moves through the venturi device 242 during operation.

According to the illustrated embodiment, the tortuous passage 276 is helical and makes at least two full revolutions about the central axis $A_2$. It is appreciated, however, that the tortuous passage 276 may take on a variety of different forms. For example, the tortuous passage 276 may include a curvilinear path that at least partially encircles the central axis $A_2$ as it moves from the inlet 272 toward the outlet zone 274. In other instances, the tortuous passage 276 may include a path with a plurality of straight segments angled relative to each other to provide a number of turns. In still other instances, the tortuous passage 276 may include a path that combines linear and non-linear path segments. The cross-sectional shape of the tortuous passage 276 may also vary along the tortuous passage 276. For example, a cross-sectional profile of at least a portion of the tortuous passage 276 may narrow in a downstream direction, that is in a direction from the inlet 272 toward the outlet zone 274. This narrowing of the tortuous passage 276 may further assist in refining the composition of the diffused liquid to include only the finest of liquid particles.

Irrespective of particular configuration, the tortuous passage 276 follows a non-linear path that, among other things, assists in preventing liquid 211 from leaking from the cartridge 200 when the cartridge 200 is upended. For example, if the cartridge 200 is temporarily held upside down, the tortuous passage 276 will assist in slowing the progression of liquid 211 within the cartridge 200 toward the outlet zone 274 and hence the outlet 214 of the cartridge 200. In this manner, the cartridge 200 can be subsequently righted without the loss of fluid. Moreover, in the event the cartridge 200 is upended and comes to rest on its side, the cartridge 200 is configured such that the volume of liquid 211 supplied with the cartridge 200 will not rise above the central axis $A_2$ of the cartridge 200. In this manner, the tortuous passage 276 will prevent the liquid 211 from spilling out of the outlet 214 as the liquid 211 will be unable to move through the entirety of the tortuous passage 276 as at least a portion of the tortuous passage 276 will be located above the fluid level of the liquid 211.

With reference again to FIG. 8, it will be appreciated that the housing 210 and internal components of the cartridge 200 define a plurality of distinct chambers downstream of the venturi device 242 through which the diffused liquid sequentially travels before being discharged from the cartridge 200 and ultimately into a surrounding environment. More particularly, the upper portion 246 of the diffusion head 240 and a lower portion of the insert 270 define a primary expansion chamber 248 immediately above the venturi device 242, a secondary chamber is provided external of the diffusion head 240 and the insert 270 within internal cavity 213 of the housing 210 above the fluid level $L_3$ of the liquid 211 to be diffused, and a tertiary chamber is provided by the tortuous passage 276 of the insert 270. Passageways or apertures 258 in the upper portion 246 of the diffusion head 240 provide fluid communication between the primary expansion chamber 248 and the secondary chamber. The upper portion 246 of the diffusion head 240 also defines a bulkhead or bulkhead portions 256 that impede the diffused liquid generated by the venturi device 242 from exiting the primary expansion chamber 248 other than through the plurality of passageways or apertures 258. The inlet 272 of the insert 270 provides fluid communication between the secondary chamber and the tertiary chamber (i.e., the tortuous passage 276). Although only one inlet 272 and one tortuous passage 276 is shown providing the sole passage for the diffused liquid to exit the cartridge 200, it is appreciated that a plurality of inlets 272 may be provide to enable diffused liquid to enter one or more tortuous passages leading to the outlet 214 of the cartridge 200. The distinct chambers described above (i.e., the primary expansion chamber, the secondary chamber and the tertiary chamber) collectively assist in refining the composition of the diffused liquid to include only the finest liquid particles as the diffused liquid moves sequentially through the chambers during operation. For instance, by the time the gas/diffused liquid mixture exits from cartridge 200, there has been some residence time in each of the distinct chambers to permit undesirably large liquid particles or droplets to precipitate or otherwise separate from the mixture and be returned to the liquid reservoir within the internal cavity 213 of the housing 210 external the diffusion head 240 for later atomization and dispersion. In this manner, the removable cartridge 200 and components thereof may provide a cartridge solution for a diffusion device which has an efficient form factor that is particularly effective at treating spaces with diffused liquid having extremely small liquid particles.

In the present disclosure, the outlet 114, 214 of the cartridge 100, 200 and/or outlet of a host diffusion device have permitted atomized liquid generated within the cartridge 100, 200 to flow directly into a space to be treated. However, the cartridge 100, 200 could alternatively direct diffused liquid into an air transport or distribution system instead. The air transport system might include ductwork or other avenues that would permit the diffused liquid to be dispersed into a remotely located space or a plurality of remotely located spaces. Thus, cartridge 100, 200 could be used to diffuse and disperse liquid throughout an entire building, for example, through the existing HVAC conduits.

It is also anticipated that cartridge 100 might be adapted to mount directly to a fitting on a conduit or source of compressed gas without the need for mounting within or as part of a host diffusion device. Such a fitting might permit cartridge 100, 200 to be positioned to treat air within a single enclosed space or may be used to treat air flowing through an air transport system and treat a plurality of spaces. Alternatively, a plurality of like cartridges 100, 200 might be used to treat individual spaces but may be linked to the same gas source. The source of compressed gas could then be controlled centrally for all of the spaces treated without the need for or provision of local controls for each treated space. Or each space could have a valve for controlling the flow of gas through the cartridge 100, 200 and thus the strength or intensity of the treatment within a particular space. Such local control valves could be then permit the same or similar cartridges 100, 200 to be used in conjunction with a common gas source to treat a plurality of different sized or configured spaces.

It may also be noted that the various diffusion devices, removable cartridges 100, 200 and components disclosed herein may include some form of operational control, such as controls for varying the pressure, velocity or timing of operation of an onboard air compressor to provide gas flow through the cartridge 100, 200. In addition to using such controls to alter the amount of liquid diffused by the devices and the corresponding degree of treatment of a space, the characteristics of the liquid to be diffused may also affect the amount of liquid diffused and the degree of treatment. For example, more viscous liquids may diffuse more slowly. The density of the liquid may also affect the degree of treatment provided. These characteristics of the cartridge 100, 200 may also be taken into account when setting controls regarding the function and operation of the diffusion devices into which the cartridges 100, 200 are received.

Moreover, the various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ features, structures, functionality or concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

This application is a continuation of U.S. patent application Ser. No. 14/835,438, filed Aug. 25, 2015, which is a continuation of U.S. patent application Ser. No. 14/612,066, filed Feb. 2, 2015, now U.S. Pat. No. 9,248,461, which claims the benefit of U.S. Provisional Application No. 61/982,504, filed Apr. 22, 2014. The entire contents of each of the foregoing applications are hereby incorporated by referenced herein.

The invention claimed is:

1. A scent dispensing system, comprising:
a liquid diffusion unit including a pressurized gas source and a control system for controlling discharge of a diffused scent containing liquid from the scent dispensing system; and
a cartridge removably received in the liquid diffusion unit, the cartridge comprising:
a cartridge receptacle comprising a plurality of pieces fixedly coupled together to define a tamperproof receptacle and having an internal cavity partially filled with a scent containing liquid to be diffused;
a venturi device within the internal cavity of the cartridge receptacle for generating the diffused scent containing liquid from the scent containing liquid contained in the internal cavity; and
a gas supply conduit that extends from a bottom end of the cartridge toward the venturi device through the scent containing liquid to be diffused to enable the venturi device to be supplied with pressurized gas from the pressurized gas source of the liquid diffusion unit via the bottom end of the cartridge.

2. The system of claim 1, wherein the plurality of pieces join together in a manner to prevent non-destructive disassembly of the cartridge.

3. The system of claim 1, wherein the venturi device is provided by a diffusion head located within the internal cavity of the cartridge receptacle.

4. The system of claim 1, wherein the cartridge includes an insert positioned above of the venturi device, the insert including an inlet to receive diffused scent containing liquid generated by the venturi device, an outlet zone from which to discharge some of the diffused scent containing liquid toward an external environment, and a tortuous passage extending between the inlet and the outlet zone.

5. The system of claim 4, wherein the tortuous passage of the insert is configured to aid in reducing an average particle size of the diffused scent containing liquid as the diffused scent containing liquid moves through the tortuous passage.

6. The system of claim 4, wherein the tortuous passage is configured to provide a convoluted flow path that retards a flow of the scent containing liquid through the insert when the cartridge is upended.

7. The system of claim 4, wherein the receptacle comprises of a lower piece and an upper piece, and wherein the venturi device and the insert are received between the lower piece and the upper piece with the insert urged into contact with the upper piece.

8. The system of claim 4, wherein a primary expansion chamber is provided between the venturi device and the insert.

9. The system of claim 8, wherein a secondary chamber is provided within the internal cavity of the cartridge receptacle and is in fluid communication with the primary expansion chamber via a plurality of apertures in a bulkhead structure.

10. The system of claim 1, wherein a plurality of chambers are provided downstream of the venturi device through which the diffused scent containing liquid sequentially moves towards an outlet of the cartridge.

11. The system of claim 10, wherein the plurality of chambers include a primary expansion chamber, a secondary chamber and a tertiary chamber.

12. The system of claim 11, wherein the primary expansion chamber is located immediately above the venturi device, the secondary chamber is radially adjacent to the primary expansion chamber and surrounds the primary expansion chamber, and the tertiary chamber is provided by a convoluted passageway that extends from the secondary chamber toward the outlet of the cartridge.

13. The system of claim 11, wherein the secondary chamber is provided above a fluid level of the scent containing liquid to be diffused and is separated from the primary expansion chamber by a bulkhead having a plurality of apertures that provide fluid communication between the primary expansion chamber and the secondary chamber.

14. The system of claim 1, wherein the pressurized gas source is an air compressor or a pump.

15. The system of claim 1, wherein the control system includes controls that are configured to permit adjustment of the timing and/or the pressure level of pressurized gas discharged from the pressurized gas source.

16. A scent dispensing system, comprising:
a liquid diffusion unit including a pressurized gas source and a control system for controlling discharge of a diffused scent containing liquid from the scent dispensing system; and
a cartridge removably received in the liquid diffusion unit, the cartridge comprising:
a cartridge receptacle including a lower portion and an upper portion that are fixedly coupled together to prevent non-destructive disassembly of the cartridge, and having an internal cavity partially filled with a scent containing liquid to be diffused;
a venturi device within the internal cavity of the cartridge receptacle for generating the diffused scent containing liquid from the scent containing liquid contained therein; and
a gas supply conduit that extends from a bottom end of the cartridge toward the venturi device through the scent containing liquid to be diffused to enable the venturi device to be supplied with pressurized gas from the pressurized gas source of the liquid diffusion unit via the bottom end of the cartridge,
wherein a plurality of chambers are provided downstream of the venturi device through which the diffused scent containing liquid sequentially moves towards an outlet of the cartridge, the plurality of chambers including a primary expansion chamber, a secondary chamber and a tertiary chamber, and
wherein the primary expansion chamber is located immediately above the venturi device, the secondary chamber is radially adjacent to the primary expansion chamber and surrounds the primary expansion chamber, and the tertiary chamber is provided by a convoluted passageway that extends from the secondary chamber toward the outlet of the cartridge.

* * * * *